US00PP15504P2

(12) United States Plant Patent
Boeder

(10) Patent No.: US PP15,504 P2
(45) Date of Patent: Jan. 25, 2005

(54) ***CHRYSANTHEMUM* PLANT NAMED 'SIZZLENESS PINK'**

(50) Latin Name: *Chrysanthemum morifolium*
Varietal Denomination: Sizzleness Pink

(75) Inventor: Mark Roland Boeder, The Hague (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 10/841,485

(22) Filed: May 10, 2004

(51) Int. Cl.[7] ..... A01H 5/00
(52) U.S. Cl. ..... Plt./292
(58) Field of Search ..... Plt./292

*Primary Examiner*—Anne Marie Grunberg
*Assistant Examiner*—Annette H Para
(74) *Attorney, Agent, or Firm*—Parkhurst & Wendel, L.L.P.

(57) ABSTRACT

A *Chrysanthemum* plant named 'Sizzleness Pink' characterized by its medium size decorative inflorescences with elongated quilled pink ray-florets, with a response time of 52 days.

3 Drawing Sheets

RELATED CULTIVARS

'Sizzleness Pink' is related to 'Sizzleness Yellow' (copending U.S. Plant patent application Ser. No. 10/841,472) and 'Sizzleness Green' (copending U.S. Plant patent application Ser. No. 10/841,484), which are all color sports of the original 'Sizzleness' (U.S. Plant patent application Ser. No. 10/782,856).

BACKGROUND OF THE INVENTION

'Sizzleness Pink' is a product of a breeding and selection program which had the objective of finding color mutants of 'Sizzleness'. The new plant of the present invention comprises a new and distinct cultivar of *chrysanthemum* plant that is a natural occurring sport of a parent *chrysanthemum* named 'Sizzleness'. A comparison with Parent *chrysanthemum* 'Sizzleness' is also made in this application. The new cultivar was discovered as a whole plant mutation in 2002 by Mark Roland Boeder in a controlled environment (greenhouse) in Rijsenhout Holland. The first act of asexual reproduction of 'Sizzleness Pink' was accomplished when vegetative cuttings were taken from the initial selection in 2002 in Rijsenhout Holland.

SUMMARY OF THE INVENTION

The present invention is a new and distinct variety of *chrysanthemum* bearing medium sized decorative blooms with elongated quilled pink ray-florets and a green center.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
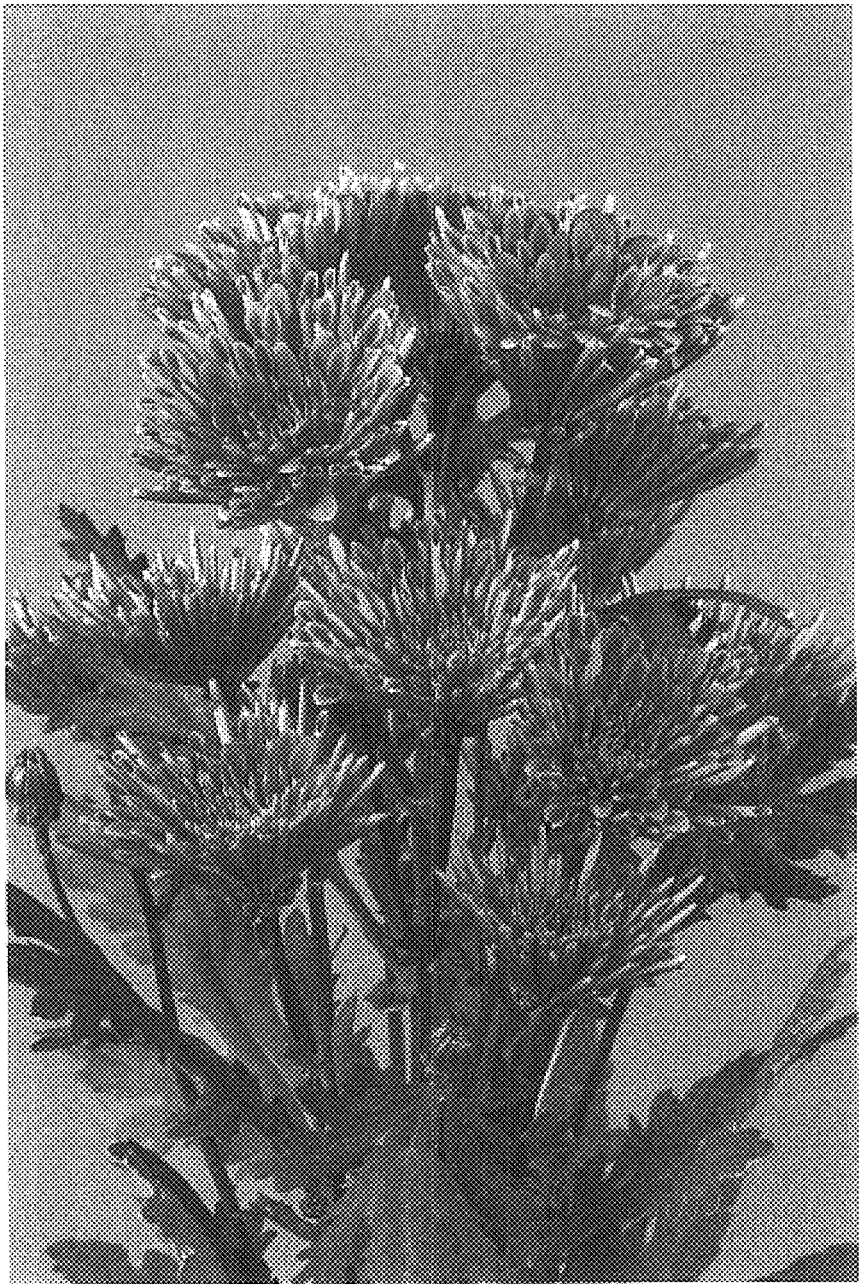
FIG. 1 shows a plant of the cultivar in full bloom.
Figure 2:
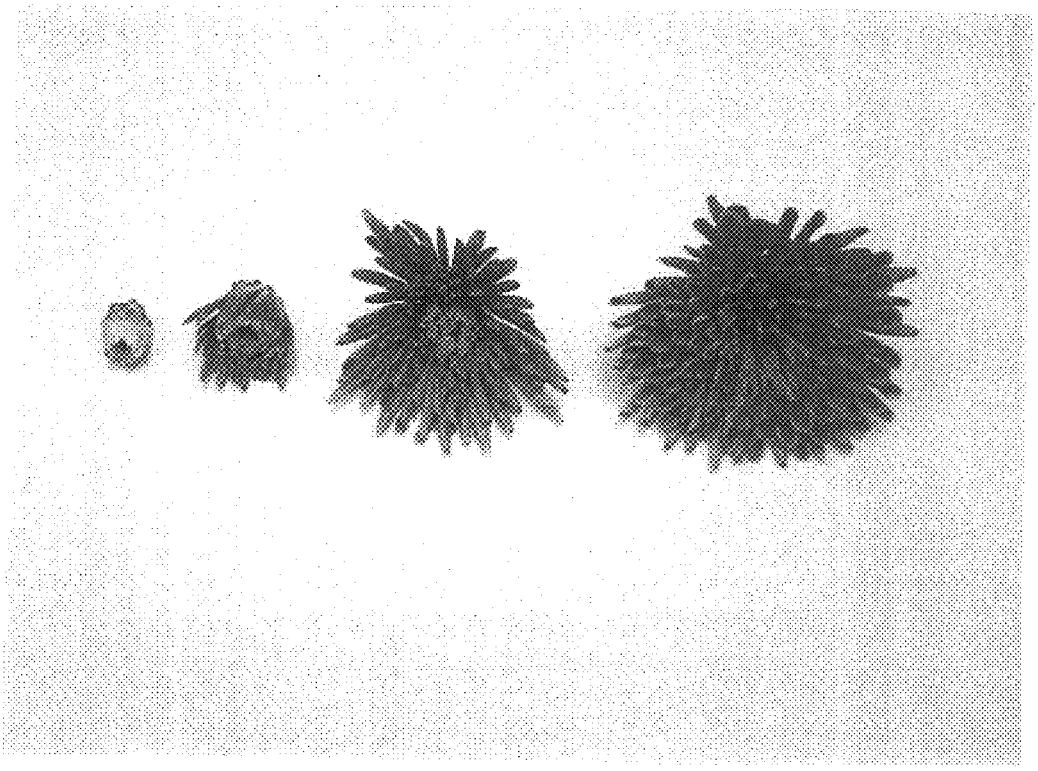
FIG. 2 shows the various stages of bloom of the new cultivar.
Figure 3:
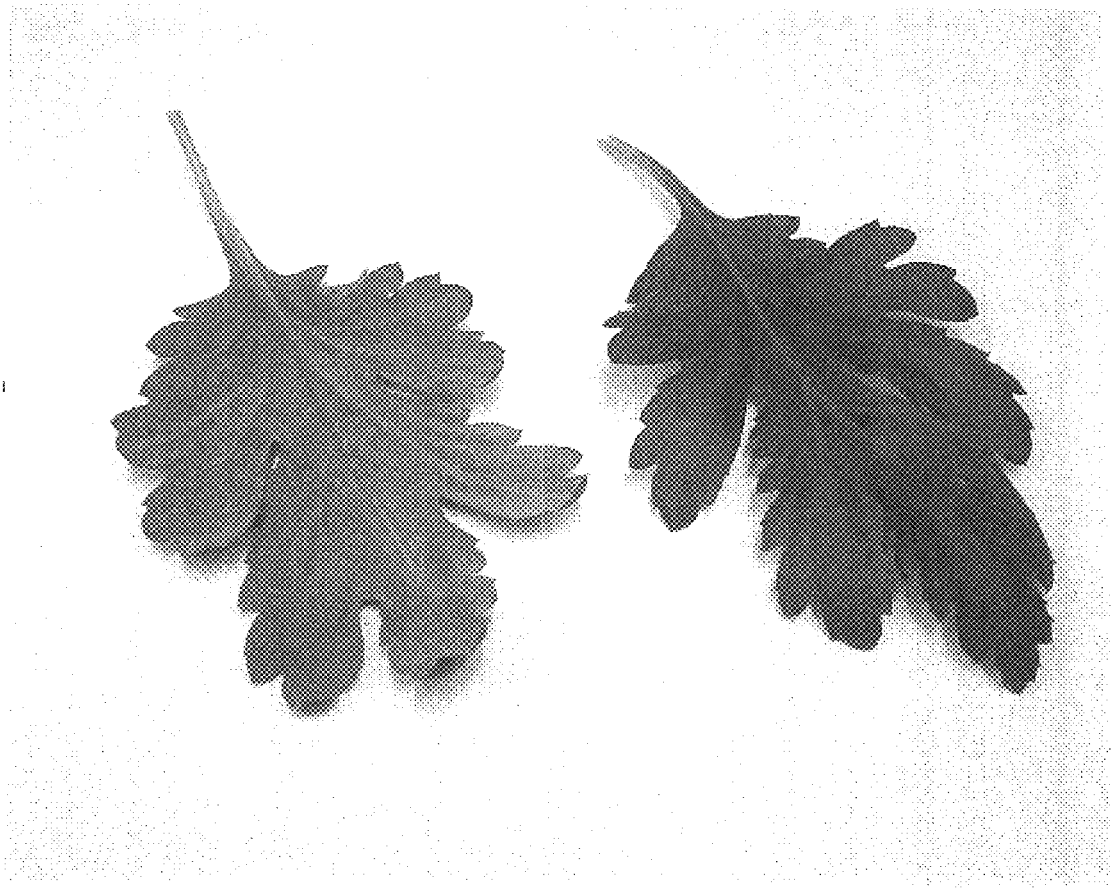
FIG. 3 shows the foliage of the new cultivar.

This new variety of *chrysanthemum* is of the botanical classification *Chrysanthemum morifolium* L. The observations and measurements were gathered from plants grown in April/May in a greenhouse in Rijsenhout Holland in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 52 days. After the long day period to flowering growth retardants were applied 2 to 3 times in an average dose of 2.5 gram/liter water. No tests were done on disease or insect resistance of susceptibility. No tests were done on cold or drought resistance. This new variety produces medium sized blooms with pink ray-florets and blooming on the plant for 5 weeks. This new variety of *chrysanthemum* has been found to retain its distinctive characteristics throughout successive propagations however the phenotype may vary significantly with variations in environment such as light intensity and temperature. To show the phenotype as described 'Sizzleness Pink' can be planted without assimilation lightning (high pressure sodium lamps) between week 1 and week 35 year under greenhouse conditions in Holland. With assimilation light (minimum level 2500 lux) it can be planted year round under greenhouse conditions in Holland.

From the cultivars known to inventor the most similar existing cultivars in comparison to 'Sizzleness Pink' is the parent 'Sizzleness' and the sport 'Sizzleness Yellow'. When 'Sizzleness Pink', 'Sizzleness Yellow' and the parent 'Sizzleness' are being compared the following differences and similarities are noticed: The difference of 'Sizzleness', and its sports 'Sizzleness Yellow' and 'Sizzleness Pink' is (1) Color ray florets. The color is for 'Sizzleness' purple and cream, while it is purple/yellow for 'Sizzleness Yellow' and pink for 'Sizzleness Pink'. For which characteristics 'Sizzleness Pink' has been selected from the original 'Sizzleness'. All other characteristics of 'Sizzleness' and 'Sizzleness Pink' are similar.

The following is a description of the plant and characteristics that distinguish 'Sizzleness Pink' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

| Botanical Description of cultivar 'Sizzleness Pink' | |
|---|---|
| Bud | |
| Size | Medium, cross-section 0.6 cm, height 0.6 cm |
| Outside color | Yellow-white 158D |
| Involucral bracts | 2 rows, length 7 mm, width 3 mm |
| Involucral bracts among disc-florets | Not present |
| Involucral bracts color | Green 138B |
| Inflorescence | |
| Type | Decorative |
| Height | 3 cm |
| Size | Medium |
| Fully Expanded | 6 cm |
| Peduncle length | Near the top 7 cm, near the middle 10 cm, near the bottom 15 cm. |
| Peduncle color | Green 138B |
| Number of inflorescences per stem | Average of 20 |
| Performance on the plant | 5 weeks |
| Seeds (if crossed) | Produced in small quantities, oval shaped, grey-brown 199A, 2 mm in length. |
| Fragrance | Typical *chrysanthemum* |
| Color | |
| Center of the flower | Immature Yellow-green 145B<br>Mature Yellow-green 154C |
| Color of upper surface of the ray-florets | Upper surface Red-purple 70B<br>Lower surface Red-purple 70D |
| Tonality from Distance | A spray mum with pink flowers and a green disc |
| Color of the upper surface of the ray florets after aging of the plant | Red-purple 70B |
| Ray florets | |
| Texture | Upper and under side smooth |
| Number | 100 |
| Shape | Elongated quilled |
| Longitudinal axis of majority | Straight |
| Length of corolla tube | Long; 2 cm |
| Ray-floret margin | Entire |
| Ray-floret length | 2.5 cm |
| Ray-floret width | 0.2 cm |
| Ratio length/width | High |
| Shape of tip | Rounded |
| Disc florets | |
| Disc diameter | 0.8 cm |
| Distribution of disc florets | Few, only visible in mature stage of flowering. |
| Shape | Tubular |
| Color | Yellow-green 154D |
| Receptacle shape | Domed raised |
| Reproductive Organs | |
| Stamen (present in disc florets only) | Thin |
| Stamen color | Yellow-green 144B |
| Pollen | Produced in small quantity |
| Pollen color | Yellow-orange 14A |
| Styles (present in both ray and disc florets) | Thick |

TABLE 1-continued

| Botanical Description of cultivar 'Sizzleness Pink' | |
|---|---|
| Style color | Yellow-green 150C |
| Style Length | 4 mm |
| Stigma color | Yellow-green 145D |
| Stigma Width | 1 mm |
| Ovaries | Enclosed in perianth |
| Plant | |
| Form | A spray mum meant for erect culture |
| Growth habit | Upright |
| Growth rate | Medium vigor |
| Height | 90 cm |
| Width | 28 cm |
| Internode length | 2–3.5 cm |
| Spray formation | Cylindrical |
| Stem Color | Yellow-green 148A |
| Stem Strength | Strong |
| Stem Brittleness | Not brittle |
| Stem Anthocyanin Coloration | Present |
| Flowering Response (photo-periodic controlled crop, not natural season) | 52 Days |
| Foliage | |
| Color immature stage | Upper side Green 137B<br>Under side Green 138C |
| Color mature stage | Upper side Green 137A<br>Under side Green 138A |
| Color midvein | Upper side Yellow-green 145C<br>Under side Yellow-green 148C |
| Size | Medium; length 13–11 cm, width 6 cm |
| Quantity (number per single stem) | 26–30 |
| Shape | Elliptic |
| Texture upper side | Fleshy and glabrous |
| Texture under side | Pubescent |
| Venation arrangement | Palmate |
| Shape of the margin | Dentate |
| Shape of Base of Sinus Between Lateral Lobes | Diverging |
| Margin of Sinus Between Lateral Lobes | Rounded |
| Shape of Base | Obtuse |
| Apex | Mucronulate |
| Petiole length | 2 cm |
| Petiole color | Yellow-green 145C |

TABLE 2

| Differences with the comparison Varieties | | | |
|---|---|---|---|
| | 'Sizzleness Pink' | 'Sizzleness Yellow' | 'Sizzleness' |
| Color ray-florets | Red-purple 70B | Greyed-red 182B with Yellow 10A at edges | Purple-violet 80C and Yellow 4D at edges |

I claim:

1. A new and distinct variety of *chrysanthemum* plant as described and illustrated.

* * * * *